United States Patent [19]

Chen

[11] Patent Number: 4,965,193

[45] Date of Patent: Oct. 23, 1990

[54] DETECTION OF MICROBIAL BETA-LACTAMASE

[75] Inventor: Kirk C. S. Chen, Seattle, Wash.

[73] Assignee: Washington Research Foundation, Seattle, Wash.

[21] Appl. No.: 114,696

[22] Filed: Oct. 29, 1987

Related U.S. Application Data

[63] Continuation-in-part of Ser. No. 638,012, Aug. 8, 1984, Pat. No. 4,740,459.

[51] Int. Cl.$^5$ .............................................. C12Q 1/34
[52] U.S. Cl. ........................................ 435/18; 435/32; 435/29
[58] Field of Search ..................... 435/18, 29, 32, 33, 435/34, 39, 184, 188, 805; 436/172

[56] References Cited

U.S. PATENT DOCUMENTS

| | | | |
|---|---|---|---|
| 4,536,334 | 8/1985 | Surayawa et al. | 540/200 |
| 4,668,620 | 5/1987 | Armenta et al. | 435/7 |
| 4,740,459 | 4/1988 | Chen et al. | 435/18 |

FOREIGN PATENT DOCUMENTS 54-001693  1/1979  Japan .

8002295  10/1980  PCT Int'l Appl. .

*Primary Examiner*—Sam Rosen
*Attorney, Agent, or Firm*—Seed and Berry

[57] ABSTRACT

An improved developer for a method for the specific detection of the presence of beta-lactamase from microbial sources is disclosed. The method utilizes a beta-lactam ring-containing substrate whose amide bond is hydrolyzed in the presence of beta-lactamase. A substrate which includes a beta-lactam antibiotic with an acyl side chain containing an alpha-amino group and an alpha-phenyl group or its derivatives is first contacted with an organism thought to produce beta-lactamase or a cell-free beta-lactamase preparation, and, subsequently, it is determined whether the reaction product between the unhydrolyzed substrate, the end products and the organism or the preparation fluoresces. Fluorescence is the indication of $\beta$-lactamase activity. The developer comprises the addition of an oxidizing agent (preferably also containing formaldehyde) to the reaction product to enhance the fluorescence. The oxidizing agent is selected from the group consisting of $Ag^+$, $Hg^{++}$, $H_2O_2$, $I_3^-$, $IO_4^-$, persulfate, $Pd^{++}$, p-hydroxymercuribenzoate, and mixtures thereof.

7 Claims, 11 Drawing Sheets

Incubation of APC with twofold dilutions of bacterial suspension from a strain of PPNG at 37°C and 50°C

DETECTION OF MICROBIAL BETA-LACTAMASE

The invention described herein was made in the course of work under Public Health Service Research Program Project Grant AI-12192 from the National Institutes of Health.

CROSS-REFERENCE TO RELATED APPLICATION

This is a continuation-in-part of U.S. patent application Ser. No. 638,012, filed Aug. 6, 1984, now U.S. Pat. No. 4,740,459.

TECHNICAL FIELD

This invention relates to an improved developer for a method for the specific detection of the presence of beta-lactamase from microbial sources and to a method of differentiating penicillinase activity from cephalosporinase activity, and distinguishing $\beta$-lactamase activity from acylase activity.

BACKGROUND ART

Beta-lactamases hydrolyze the amide bonds of the beta-lactam ring of sensitive penicillins and cephalosporins, are widely distributed among microorganisms, and play an important role in microbial resistance to beta-lactam antibiotics. Several methods for detecting the presence of microbial beta-lactamase have been developed. For example, chemical methods for the detection of the enzymatic hydrolysis of the beta-lactam ring include: (a) the acidimetric method, which employs a pH color indicator to detect the decrease in pH resulting from the formation of a new carboxyl group; (b) the iodometric method, which is based on the decolorization of a starch-iodine complex by the end products of beta-lactamase hydrolysis, which act as reducing agents to reduce iodine in the complex; and (c) the chromogenic cephalosporin method, which is based on a color change following the hydrolysis of a chromogenic cephalosporin substrate (R. B. Sykes and K. Bush, "Physiology, Biochemistry and Inactivation of Beta-lactamases," *Chemistry and Biology of Beta-lactam Antibiotics* 3: 155-207 (1982) R. B. Morin and M. Gorman (eds.), Academic Press, New York. An alternative to the chemical methods is a microbiological assay method which is based on the loss of antibacterial activity following the hydrolysis of the beta-lactam ring.

Microbial acylases which remove the acyl side chains of susceptible penicillins or cephalosporins are also produced by many microorganisms. The cleavage of acyl side chains from beta-lactam antibiotics often results in a decrease in pH and reduction of antibiotic activity. Acidimetric and microbiological methods may not differentiate $\beta$-lactamase activity from acylase activity.

Although microbial beta-lactamases do not act exclusively on penicillins or on cephalosporins, many show a predominance of penicillinase or cephalosporinase activity. Thus, chemical or microbiological methods which utilize a single beta-lactam substrate cannot differentiate penicillinase activity from cephalosporinase activity and often give a false, negative result for beta-lactamase activity.

There exists a need for a method which differentiates penicillinase activity from cephalosporinase activity and distinguishes between beta-lactamase and acylase activity.

The aforementioned co-pending U.S. patent application discloses and claims a method for detecting the presence of beta-lactamase activity from microbial sources using a fluorescence assay. It is desirable to provide means to enhance the fluorescent signal generated in said assay in order to increase the sensitivity of the assay. Additionally, it is desirable to provide improved methodologies for decreasing the time of the assay. The prior art teaches the use of a buffered solution containing formaldehyde in order to enhance fluorescent development of said assay (Taylor, D. N., K. C. S. Chen, K. Panikabutra, C. Wongba, A. Chitwarkern, P. Echeverria, and K. K. Holmes, *Lancet* ii: 625-626 (1985)). This use of a formaldehyde solution as a fluorescence developer was described in a subsequent article by K. C. S. Chen and K. K. Holmes (*J. Clin. Microb.* 23: 539-544 (1986)).

Despite the increase in sensitivity achieved by the formaldehyde developer solution, there exists a need for greater sensitivity in order to expand the applicability of the assay. The present invention fulfills this need.

DISCLOSURE OF THE INVENTION

Briefly stated, the present invention comprises a method for increasing the sensitivity of an assay for detecting the presence of beta-lactamase from microbial sources. Specifically, agents are described that yield, relative to formaldehyde, a greater enhancement of the fluorescence developed by end products produced by beta-lactamase hydrolysis of beta-lactam-containing compounds.

The method includes the steps of contacting a substantially nonfluorescent, beta-lactam ring-containing substrate with an organism thought to produce beta-lactamase, or a cell-free preparation thought to contain beta-lactamase; subsequently contacting the reaction mixture formed therefrom with a fluorescence developer solution comprising an oxidizing agent in buffer to form a reaction product; and determining whether the reaction product fluoresces. Preferably, the fluorescence developer solution also contains formaldehyde. Fluorescence is the indicator of the presence of beta-lactamase.

The substantially nonfluorescent substrate may include a beta-lactam antibiotic with an acyl side chain containing an alpha-amino group and an alpha-phenyl group or its derivatives, such as cyclohexyl or cyclohexenyl. For example, the acyl side chain of the beta-lactam antibiotic may contain a D(—)$\alpha$-phenylglycyl group, such as ampicillin, cephalexin or cephaloglycin (phenyl group without substitution), or a D(—)p-hydroxyphenylglycyl group, such as amoxicillin or cefadroxil (phenyl group with hydroxyl group substitution). The substrate may also be a compound with a beta-lactam ring structure with comparable alpha-amino and alpha-phenyl groups, such as hetacillin.

Alternatively, the substrate may include a beta-lactam-containing compound which does not exhibit antibiotic properties. Such compounds need only have an acyl side chain containing an alpha-amino group and an alphaphenyl group or its derivatives.

As used herein, the term "substantially nonfluorescent substrate" is used to indicate the aforementioned category of substrates, which may possess a low-level background fluorescence but are still capable of being employed in the present invention because the background level of fluorescence does not interfere with the fluorescence assay.

Preferably, oxidizing agents are selected from the group consisting of $Ag^+$, $Hg^{++}$, $H_2O_2$, $I_3^-$, $IO_4^-$, persulfate, $Pd^{++}$, p-hydroxymercuribenzoate, and mixtures thereof. Additionally, these oxidizing agents mix with formaldehyde.

Preferred buffers are salts of acids selected from the group consisting of citric acid, tartaric acid, malic acid, succinic acid, glutaric acid, phthalic acid, and lactic acid. Most preferably, the salts of acids are sodium or potassium salts of acids.

Preferably, the method is conducted at a pH ranging from about 3.5 to about 5.5, and is performed at a temperature ranging from between about 22° C. to about 50° C.

BEST MODE FOR CARRYING OUT THE INVENTION

Figure 1:
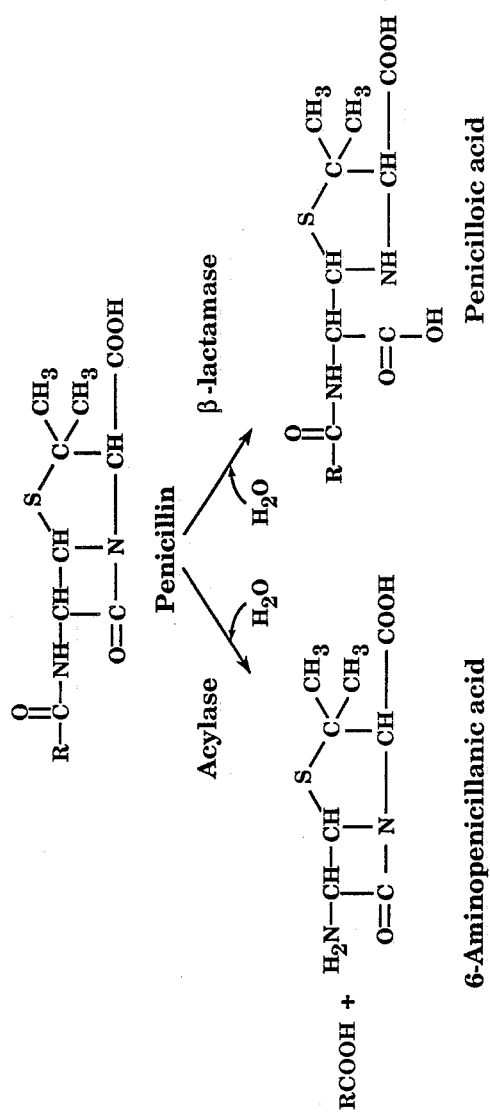
FIG. 1 diagrammatically illustrates the hydrolysis of penicillins by acylase and beta-lactamase.
Figure 2:
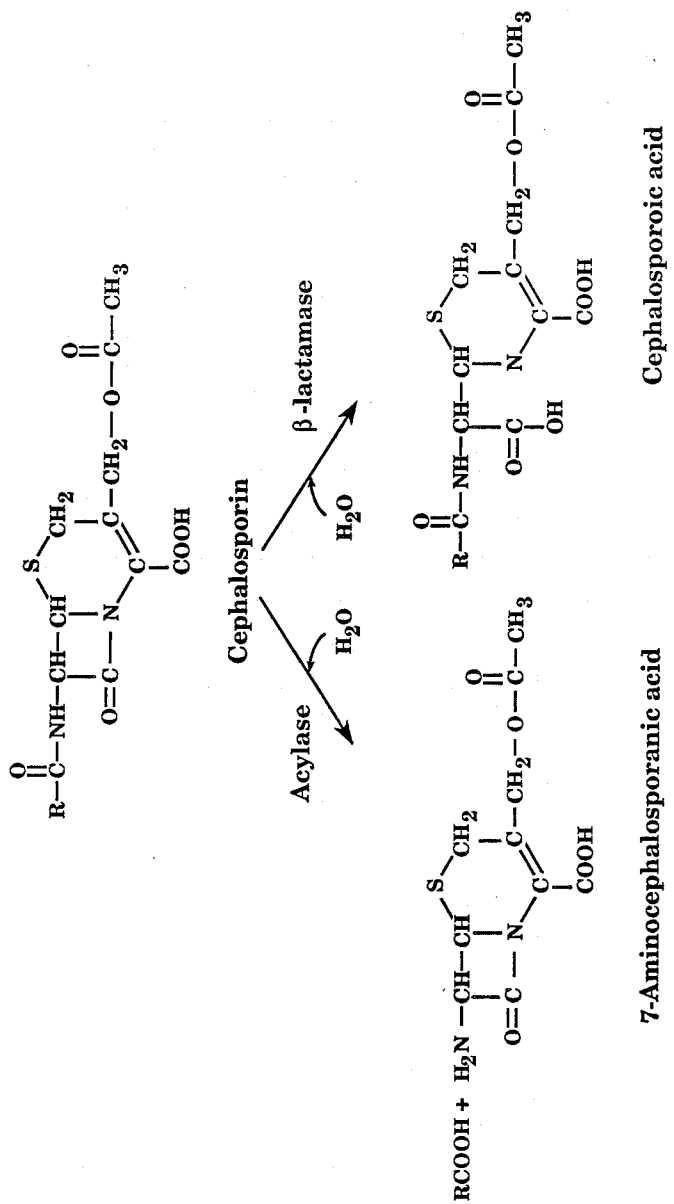
FIG. 2 diagrammatically illustrates the hydrolysis of cephalosporins by acylase and beta-lactamase.

This invention provides a method for increasing the sensitivity of an assay for the detection of microbial beta-lactamases by using an improved developer which consists of a mild oxidizing agent that yields a greater enhancement of fluorescence development than that achieved by use of formaldehyde alone. Preferably, the improved developer (also called developer II) also contains formaldehyde. This greater sensitivity allows for direct detection of beta-lactamases in cultures and in clinical specimens. The latter group includes infected body fluids, such as sera, urethral exudates, vaginal fluids, cervical fluids, pus or cerebrospinal fluid. For example, when the prior art formaldehyde developer solution was used for detection of penicillinase-producing *Neisseria gonorrhoeae* (PPNG) in cervical fluids, a large portion of the test results were false-negative, indicating that the developer solution was not sufficiently sensitive. By contrast, the developers of the present invention generate relatively few false-negative results.

The present invention provides a more sensitive and less expensive method for detecting microbial beta-lactamases which can not only differentiate penicillinase from cephalosporinase activity but can also differentiate beta-lactamase activity from acylase activity. Some penicillins and cephalosporins, such as ampicillin and cephalexin, yield fluorescent end products after hydrolysis by beta-lactamase. Further, these fluorescent end products can be detected on filter paper under long-wave ultraviolet light after brief heating.

Consistent with these findings, the assay of the aforementioned co-pending application for the detection of microbial beta-lactamases with a predominance of either penicillinase or cephalosporinase activity may be initiated by: (a) incubating an amount of a solution of a beta-lactam antibiotic such as ampicillin or cephalexin, or other beta-lactam containing a side chain with an alpha-amino group and an alpha-phenyl group, with or without various substitutions, with a test microorganism thought to produce beta-lactamase or a cell-free beta-lactamase preparation; (b) placing a drop of that solution on a surface such as filter paper; (c) briefly heating the filter paper; and (d) exposing the filter paper to ultraviolet light.

Other beta-lactams which may be utilized include amoxicillin, cephaloglycin, and cefadroxil.

Suitable surfaces with low background fluorescence other than filter paper include paper towels, sheets of nitrocellulose, cellulose acetate, silica gel and polyamide.

This method may be used to detect predominant penicillinase activity (e.g., using ampicillin or amoxicillin as the substrate) or cephalosporinase activity (e.g., using cephalexin, cefadroxil or cephaloglycin as the substrate). Beta-lactamase activity towards ampicillin and cephalexin generates end products (D-phenylgylcylpenicilloic acid and D-phenylglycyldeacetoxycephalosporoic acid) that can be developed into fluorescent species by this method. Acylase activity, however, produces nonfluorescent end products (D(−)α-aminophenylacetic acid and 6-aminopenicillanic acid or 7-aminodeacetoxycephalosporanic acid) that cannot be developed into fluorescent species by this method. Thus, as shown in FIGS. 1, 2, 5 and 6, beta-lactamase activity may be distinguished from acylase activity.

The presence of acylase in the reaction mixture does not interfere with the detection of beta-lactamase using this fluorescent method. By using beta-lactam substrates representing both penicillin and cephalosporin antibiotics, the specificity of beta-lactamases of various species of gram-positive and gram-negative organisms can be determined.

An alternative method employing an overlay which has been impregnated with the substrate, contacted with the bacteria on the surface of a culture medium, incubated, and then viewed under a long-wave ultraviolet light lamp to detect the fluorescence has also been developed, permitting the detection and differentiation of the fluorescence end product from the natural fluorescence of the bacteria without the need for removing the bacteria from the milieu through centrifugation, while in addition allowing the detection of enzyme activity by many individual colonies on one plate.

The present invention teaches that the fluorescence produced by the end products of $\beta$-lactamase hydrolysis can be enhanced by utilization of a developer solution containing an oxidizing agent selected from the group consisting of $Ag^+$, $Hg^{++}$, $H_2O_2$, $I_3^-$, $IO_4^-$, persulfate, $Pd^{++}$, p-hydroxymercuribenzoate, and mixtures thereof. Preferably, the developer solution also contains formaldehyde.

Ampicillin, cephaloglycin and cephalexin have the common acyl side chain, $D(-)-\alpha$-aminophenylacetic acid and the intact $\beta$-lactam nuclei 6-aminopenicillanic, 7-aminocephalosporanic acid and 7-aminodeacetoxycephalosporanic acid, respectively. Amoxicillin and cefadroxil have the common acyl side chain $D(-)$-P-hydroxylphenylglycine and the intact $\beta$-lactam nuclei, 6-aminopenicillanic acid and 7-aminodeacetoxycephalosporanic acid, respectively. In this assay, the end products of acylase activity upon ampicillin, cephaloglycin, cephalexin, amoxicillin, and cefadroxil are not fluorescent after reaction with the improved fluorescence developer as described in this invention, only the end products of the beta-lactamases become fluorescent. Therefore, the present invention can not only detect and distinguish penicillinase and cephalosporinase activity of $\beta$-lactamase, but it can also differentiate $\beta$-lactamase activity from acylase activity.

The fluorescence can be revealed by spotting the reaction mixture on filter paper under a long-wave UV light. Alternatively, the fluorescence can be observed directly in solution or measured fluorimetrically using appropriate excitation and emission wavelengths, for example, 350 nm as the excitation wavelength and 425 nm as the emission wavelength.

Alternatively, the aforementioned oxidizing agents can be mixed with formaldehyde. The formaldehyde concentration in the improved fluorescence developer can range from approximately 0.22M to approximately 2.2M. The concentration of a mild oxidizing agent in the improved fluorescence developer can range from approximately 0.22 mM to 2.2 mM. Where $Hg^{++}$ ion is used in the improved fluorescence developer of the present invention, sulfhydryl—containing compounds may interfere with the assay. Additionally, where the $Ag^+$ ion is employed, the presence of sulfhydryl groups and chloride ions can also interfere. Therefore, concentration of these cations must be increased accordingly.

Sensitivity of the beta-lactam assay can be enhanced approximately 40-fold and 100-fold, respectively, for ampicillin and cephalexin substrates over the prior art, thus permitting more sensitive assays to be conducted. For example, detection of penicillinase-producing *Neisseria gonorrhoeae* (PPNG) in cervical fluids can be achieved utilizing the detection system employing the improved developer of the present invention.

Two tubes are utilized in the PPNG assay. The first tube contains ampicillin substrate; the second tube contains ampicillin plus methicillin. Beta-lactamase activity of PPNG is completely inhibited by methicillin, while beta-lactamase activity from vaginal and cervical flora, such as *Bacteroides bivius*, are not inhibited by methicillin. Therefore, if both tubes prove positive for beta-lactamase activity, a false-positive result is possible. However, if ampicillin only is positive and the second tube containing ampicillin plus methicillin is negative, then PPNG is confirmed to be positive. Prior art methodologies lacked sufficient sensitivity to perform such a diagnosis.

It will be appreciated by those skilled in the art, through reference to the examples which follow, that slight variations on the assay disclosed will readily exist, depending, for instance, on the activity of the enzyme and the sample being tested.

For example, the reaction mixture composed of the source of beta-lactamase suspended only in the ampicillin substrate may be examined very soon after mixing for fluorescence produced by plasmid-mediated beta-lactamases (e.g., penicillinase-producing *Neisseria gonorrhoeae, Haemophilus influenzae*), or may be incubated with either ampicillin or cephalexin for a longer period of time prior to determination of fluorescence produced by inducible beta-lactamases or by weak beta-lactamase producers. Further, when fluorescence developer is used, there is some flexibility in the choice of the time and the temperature of hydrolysis.

To summarize the examples which follow: Example I is for the detection of open beta-lactam ring end products, accomplished utilizing the rapid detection method, or spot test, of the parent application, confirming the spot test results with a high-voltage electrophoresis (HVE) test, and then also confirming the spot test by the nitrocefin test. Example II compares the fluorescence of the prior art assay with the assay by the use of the improved developer of the present invention.

The results obtained through the use of these procedures revealed that (1) beta-lactamase may be detected through identification of fluorescent end products utilizing the spot test without the necessity of electrophoretic separation of the substrates and end products; (2) the spot test proved to be more sensitive than the nitrocefin test, especially for gram-positive microorganisms; (3) the rapid detection method, or spot test, can be utilized to differentiate between penicillinase and cephalosporinase activities, as well as differentiating beta-lactamase activities from acylase activities; (4) the spot test provides a means of semiquantitatively determining the amount of beta-lactamase activity from a microbial source; and (5) the spot test method may be utilized to determine the specificity of beta-lactamases of various species of gram-positive and gram-negative bacteria.

The following examples are offered by way of illustration and not by way of limitation.

EXAMPLE I

Materials

Chemicals

Compounds (acid forms) related to beta-lactam antibiotics, including the acyl side chain and the beta-lactam nuclei, were purchased from Sigma Chemical Co., St. Louis, Mo., and separately dissolved in 0.04M sodium phosphate buffer, pH 7.5, to a final concentration of 0.02M, except for amoxicillin (0.01M, prepared in 0.02M sodium phosphate buffer) and $D(-)\alpha$-aminophenylacetic acid (0.005M, prepared in 0.01M sodium phosphate buffer). Nitrocefin was obtained from Glaxo Research Ltd., Greenford, Middlesex, England, and was prepared and used at a concentration of 50 ug/ml. (Sykes, R. B., and K. Bush, "Physiology, Biochemistry, and Inactivation of Beta-lactamases", *Chemistry and Biology of Beta-lactam Antibiotics* 3: 155–207, R. B.

Morin and M. Gorman (eds.), Academic Press, New York, 1982).

Methods

Preparation of Inocula for Detection of Beta-lactamase

*Haemophilus ducreyi* and *H. influenzae* were grown on GC agar base (BBL Microbiology Systems, Cockeysville, Md.) with supplements, as described in Totten, P. A., H. H. Handsfield, D. Peters, K. K. Holmes, and S. Falkow ("Characterization Ampicillin-Resistant Plasmids from *Haemophilus ducreyi*," *Antimicrob. Agents Chemother.* 21: 622-627 (1982). Bacteroides spp. were grown anaerobically on Columbia base agar (BBL) with supplements, as described in Williams, B. L., K-A. Osterberg, and J. Jorgensen, "Subgingival Microflora of Periodontal Patients on Tetracycline Therapy," *J. Clin. Periodontol.* 6: 210-221 (1979). Microorganisms from research efforts described previously by K. C. S. Chen, N. J. Culbertson, J. S. Knapp, G. E. Kenny, and K. K. Holmes in "Rapid Method for Simultaneous Detection of the Arginine Dihydrolase System and Amino Acid Decarboxylases in Microorganisms," *J. Clin. Microbiol.* 16: 909-918 (1982), were grown aerobically on GC medium base (Difco Laboratories, Detroit, Mich.) containing 1% defined supplement (White, L. A., and D. S. Kellogg Jr., "*Neisseria gonorrhoeae* Identification in Direct Smears by a Fluorescent Antibody Counterstain Method," *Appl. Microbiol.* 13: 171-174 (1965)) at 37° C. overnight, except for *Neisseria gonorhoeae*, which was grown in a $CO_2$ incubator (Totten, P. A., H. H. Handsfield, D. Peters, K. K. Holmes, and S. Falkow, "Characterization of Ampicillin-Resistant Plasmids from *Haemophilus ducreyi*," *Antimicrob. Agents Chemother.* 21: 622-627 (1982)).

Aliquots (50 ul) of each beta-lactam antibiotic were separately place in a microcentrifuge tube (200 ul; Stockwell Scientific, Monterey Park, Calif.). Approximately one-half of a loopful (diameter, 2 mm) of growth of each strain was removed from the agar plate and dispensed in each substrate by brief vortexing.

The mixture was then incubated for 5 and 15 minutes at room temperature for the rapid spot test. Uninoculated substrate controls were prepared in the same manner.

Concurrently, the mixture of the strain and each substrate was incubated for 1 hour at 37° C. Uninoculated substrate controls were again prepared in the same manner. After incubation, the tubes (except the uninoculated substrate control tubes and tubes for the rapid spot test) were centrifuged in a Microfuge (model 152; Beckman Instruments, Inc., Fullerton, Calif.) for 1 minute.

Detection of Open Beta-lactam Ring End Products by the Rapid Detection Method

After 1 hour of incubation at 37° C., a 5 ul volume of supernatant for each tube, including each uninoculated substrate control tube, was applied separately onto a Whatman 3 MM paper and heated at 120° C. in an oven for 5 minutes. The fluorescent intensity of each test spot was then compared with the control spot of its uninoculated substrate under a long-wave UV lamp and classified as negative, weakly positive, or positive.

For the rapid spot test, 5 ul of uncentrifuged bacterial suspension from each inoculated tube after incubation at room temperature for 5 and 15 minutes, and 5 ul from each uninoculated substrate control tube, were applied onto the paper and heated at 120° C. for 5 minutes. For microorganisms which showed strong autofluorescence (e.g., Pseudomonas spp.), the tip of an Eppendorf pipettor containing 5 ul of suspension was applied to the filter paper, allowing the fluid to be withdrawn from the tip by capillary action. This caused the bacteria to remain concentrated at the point of application, so that central bacterial autofluorescence could be differentiated from peripheral fluorescence of the end products. The fluorescent intensity of the rapid spot test was classified as described for the 1-hour spot test.

Detection of Open Beta-lactam Ring End Products by High-Voltage Electrophoresis

A 5 ul volume of supernatant from each tube after 1 hour of incubation was separately applied onto a Whatman 3 MM paper which was subjected to high-voltage electrophoresis (HVE) at pH 2.1, at 80 V/cm for 30 minutes (Chen, K. C. S., and R. M. Krause, "A Peptide Mapping Technique—A Three-Map System," *Anal. Biochem.* 69: 180-186 (1975)). The paper was dried at 90° C. for 15 minutes, and viewed under a long-wave UV lamp. The fluorescent intensity of each test was compared with that of its uninoculated substrate control and classified as negative, weakly positive, or positive. The paper was then stained with ninhydrin-cadmium acetate (Heilmann, J., J. Barrollier, and E. Watzke, "Beitrag zur Aminosaurebestimung auf Papier Chromatogrammen," *Hoppe-Seyler's Z. Physiol. Chem.* 309: 219-220 (1975)) to reveal the unhydrolyzed substrate. The color intensities of the end products were further classified as negative or as weakly, moderately or strongly positive.

Detection of Beta-lactamase by the Nitrocefin Test

The nitrocefin test (O'Callaghan, C. H., A. Morris, S. M. Kirby, and A. H. Shingler, "Novel Method for Detection of beta-lactamases by Using a Chromogenic Cephalosporin Substrate," *Antimicrob. Agents Chemother.* 1: 283-288 (1972)) is a specific rapid test available for the detection of beta-lactamase and was performed concurrently with the rapid detection method, or spot test, described herein in order to provide means for evaluating the accuracy of the spot test.

The nitrocefin test was performed under the same conditions as the spot test. Approximately one-half of a loopful of growth of each organism was dispersed in 50 ul of nitrocefin (50 ug/ml) in a well of a microtitration plate (Linbro Division, Flow Laboratories, Inc., Hamden, Conn.), and incubated for 1 hour at 37° C., or for 5 and 15 minutes at room temperature for the rapid test.

Detection of Beta-lactamase by Identification of Fluorescent End Products

In initial studies, penicillins (ampicillin and amoxicillin) and cephalosporins (cephalosporin C, cephaloglycin, cephalexin and cefadroxil) containing a primary amino group on the acyl side chain were separately incubated with *Citrobacter freundii* for 1 hour at 37° C. Supernatant from each reaction mixture was separated by HVE (high-voltage electrophoresis) at pH 2.1 (Chen, K. C. S., and R. M. Krause, "A Peptide Mapping Technique—A Three-Map System," *Anal. Biochem.* 69: 180-186 (1975)). The product and the unhydrolyzed substrate were revealed by ninhydrin-cadmium acetate stain (Heilmann, J., J. Barrollier, and E. Watzke, "Beitrag zur Aminosaurebestimung auf Papier Chromatogrammen," *Hoppe Seyler's Z. Physiol. Chem.* 309: 219-220 (1975)), after drying at 90° C. for 15 minutes. The ninhydrin-cadmium acetate stain showed distinct spots of the end product and the unhydrolyzed substrate for all beta-lactam antibiotics tested, except cephaloglycin and cephalosporin C (the end products trailed toward the cathode).

Figure 3:
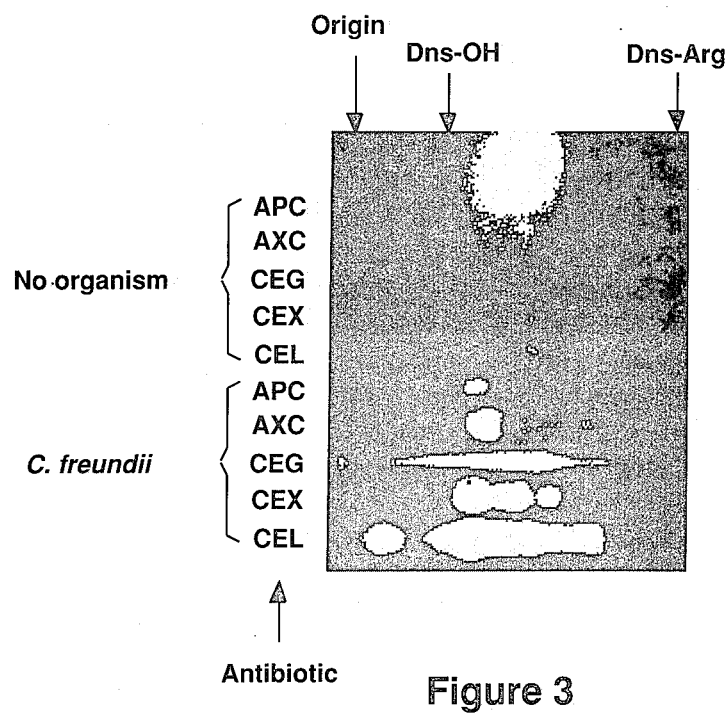
FIG. 3 depicts high-voltage electrophoretic analysis of open beta-lactam ring end products.

Subsequent studies showed that prior to ninhydrin-cadmium acetate staining, each major end product (as detected later by ninhydrin-cadmium stain; cephaloglycin produced no distinct major end product) and some minor end-products, except those from cephalosporin C, were highly fluorescent under a long-wave UV lamp, while the unhydrolyzed substrates were not fluorescent, as shown in FIG. 3. The fluorescent pattern produced by *C. freundii* for each substrate was found to be identical to that produced by purified beta-lactamase from *Enterobacter cloacae* or *Bacillus cereus* (Sigma; 100 nanomoles of each substrate incubated with 1 ug of each enzyme for 1 hour at 37° C.). Trace amounts of the fluorescent open beta-lactam-ring forms of ampicillin, amoxicillin and cefadroxil detected in the uninoculated substrate control were attributable to spontaneous hydrolysis during incubation and contamination with the open-ring forms themselves in the commercial sources, and this background of fluorescence was easily distinguished from the amount of fluorescent end product produced by the microbial beta-lactamases. The minor fluorescent end products of cephalexin and cefadroxil after incubation were presumably due to acid degradation of each major end product during HVE at pH 2.1, since better cooling of the paper during HVE reduced their formation. Therefore, all five beta-lactam substrates which produced fluorescent end products (open beta-lactam-ring forms during incubation with known beta-lactamases could be used for detection of microbial beta-lactamases.

In addition, it was also found that the end product of each beta-lactam substrate shown in FIG. 3 could be detected on the filter paper without subsequent electrophoretic separation after brief heating at 120° C. for 5 minutes. Therefore, the simple spot test described herein can be employed for the detection of microbial beta-lactamases.

Figure 4:
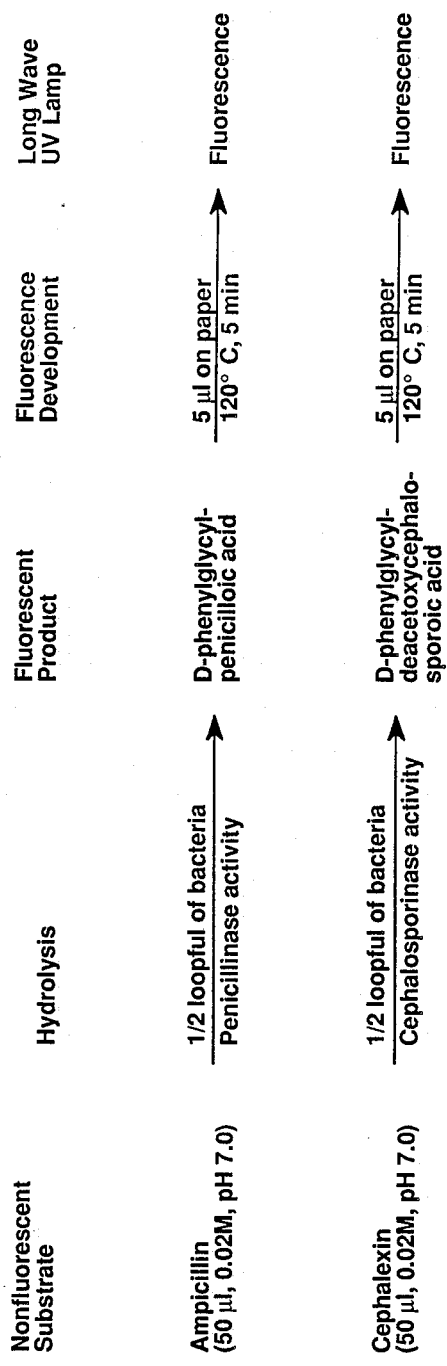
FIG. 4 is a summary of the fluorescent spot test for the detection of microbial beta-lactamases without using a fluorescence developer.

Selection of Beta-lactam Substrates for Differentiation Between Penicillinase and Cephalosporinase Activities of Beta-lactamase by the Spot Test In order to detect beta-lactamases with a predominance of penicillinase or cephalosporinase activity, and to detect weak beta-lactamase producers using the spot test, two substrates which produced the least fluorescent background (due to nonenzymatic hydrolysis during incubation and the end-product contaminants present in the commercial sources) were selected. Ampicillin produced less fluorescent background than amoxicillin, and was chosen as the substrate for penicillinase despite the fact that its open beta-lactam-ring form was less fluorescent than that of amoxicillin, as shown in FIG. 3. Likewise, cephalexin was chosen as the substrate for cephalosporinase. A summary of the fluorescent spot test method is provided in FIG. 4.

Figure 6:
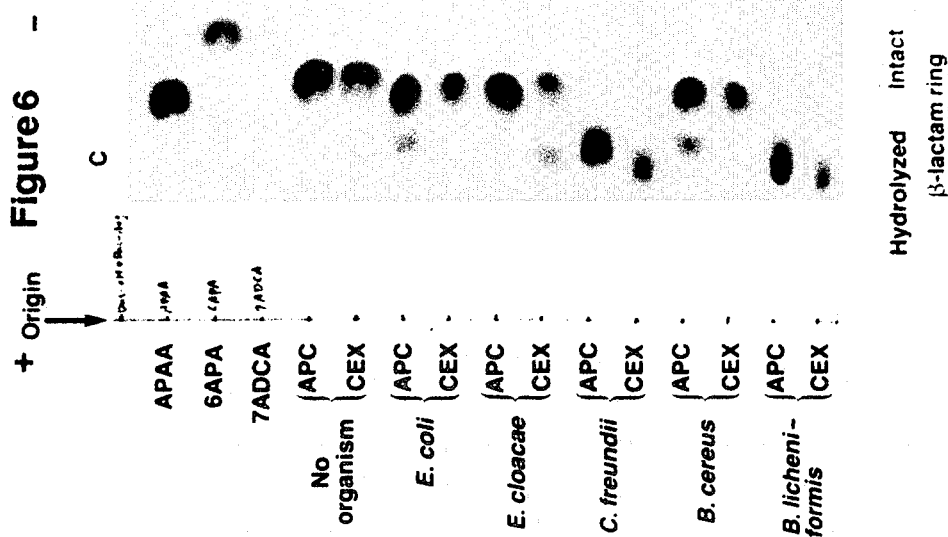
FIG. 6 illustrates the activity of beta-lactamase as depicted in FIG. 5 after ninhydrin-cadmium acetate staining.
Figure 5:
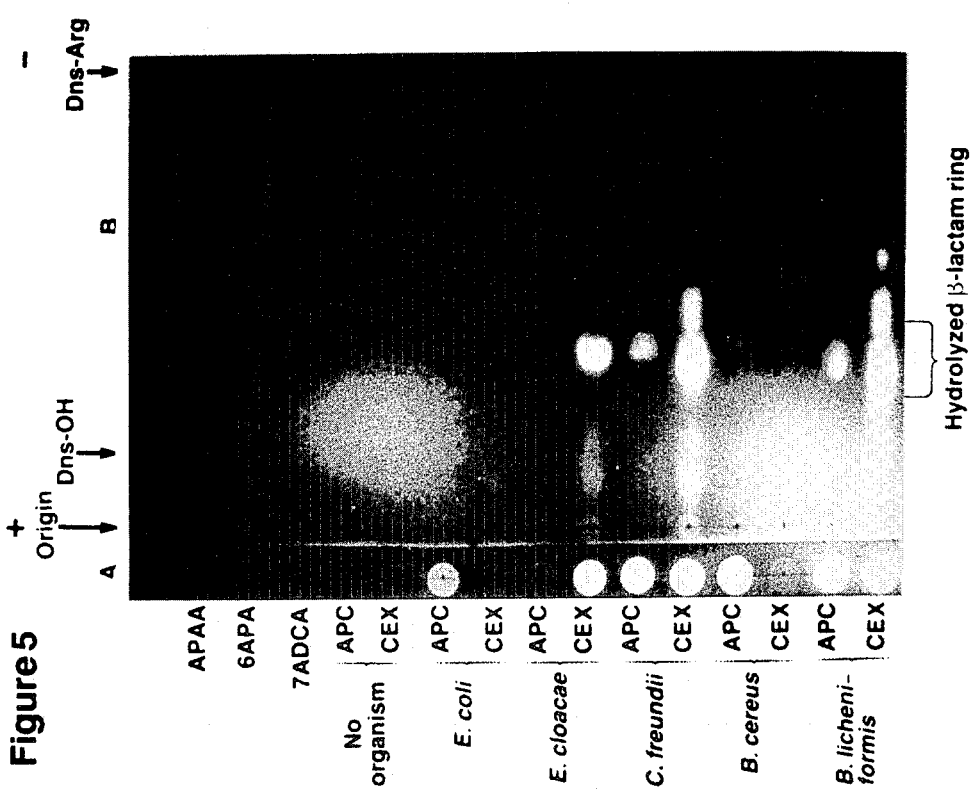
FIG. 5 illustrates the activity of beta-lactamase in *E. coli*, *E. cloacae*, *C. freundii*, *B. cereus*, and *B. licheniformis* as determined by the spot test (A) and the high-voltage electrophoresis test (B) viewed under a long-wave ultraviolet (UV) lamp.

Differentiation of Beta-lactamase and Acylase Activities by the Spot Test and HVE In order to determine whether the spot test method could distinguish beta-lactamase activity from acylase activity, the end products of acylase (100 nanomoles each, the common side chain, D(−)α-aminophenylacetic acid, and the intact beta-lactam nuclei, 6-aminopenicillanic acid, and 7-aminodeacetoxycephalosporanic acid) were separately applied onto Whatman 3 MM paper. None of the end products of acylase were fluorescent either by the spot test method or the HVE method, as shown in FIG. 5. However, all produced color after ninhydrin-cadmium acetate stain, as shown in FIG. 6. Therefore, both the spot test method and the HVE method can distinguish beta-lactamase activity from acylase activity.

Semiquantitation of Beta-lactamase Activity

The spot test result for beta-lactamase activity using a given substrate was classified as weakly positive (W) when the fluorescent intensity of the spot was faint, but discernibly greater than that of the uninoculated substrate control; and as positive (+) when bright blue-green fluorescence was observed.

The HVE test result for beta-lactamase activity using a given substrate was classified as weakly positive (W) when faint fluorescence was observed at the position corresponding to that of the end product after HVE, and the color intensity of the end-product spot after ninhydrincadmium acetate stain was slightly but discernibly greater than that of the end product in the uninoculated substrate control (produced by spontaneous nonenzymatic hydrolysis during incubation and from end product contamination of commercial sources); as moderately positive (M) when bright blue-green fluorescence was observed at the position corresponding to that of the end product, but color intensity of the end-product spot after ninhydrin-cadmium acetate stain was less than that of the remaining substrate spot; and as strongly positive (S) when bright blue-green fluorescence was observed at the position corresponding to that of the end-product spot and the color intensity of the end-product spot after ninhydrin-cadmium acetate stain was greater than that of the remaining substrate spot.

Distribution of Beta-lactamase Activities Among Representative Microorganisms

The spot test method was used for the detection of beta-lactamase produced by one strain each of *Escherichia coli*, *E. cloacae*, *C. freundii*, *B. cereus* and *B. licheniformis* using ampicillin (for penicillinase activity) and cephalexin (for cephalosporinase activity) as substrates. The results of the spot test shown in FIG. 5A were confirmed by HVE visualized under UV light, as shown in FIG. 5B, and with a ninhydrin-cadmium acetate stain, as shown in FIG. 6.

Fluorescence was produced by *E. coli* during incubation with ampicillin for 1 hour at 37° C. (FIG. 5A), and the end product (D-phenylglycylpenicilloic acid) was detected under UV light (FIG. 5B), and further confirmed by ninhydrin-cadmium acetate stain (FIG. 6). The penicillinase activity of this *E. coli* strain was determined to be weakly positive by both the spot test and the HVE method using the criteria described above, while no cephalosporinase activity was detected by either method.

The fluorescent end product was produced by *E. cloacae* during incubation with cephalexin for 1 hour at 37° C. (FIG. 5A). The end product was visualized under UV light after HVE (FIG. 5B) and further confirmed by ninhydrin-cadmium acetate stain (FIG. 6). The cephalosporinase activity of *E. cloacae* was classified as positive by the spot test and as moderately positive by the HVE method using the criteria described above; no penicillinase activity was detected by either method.

Through use of the spot test and the criteria described above, penicillinase and cephalosporinase activities of *C. freundii* and *B. licheniformis* were both classified as positive, while in *B. cereus*, the penicillinase activity was positive and cephalosporinase activity was negative (FIG. 5A). By the HVE method and the criteria described above, the penicillinase and cephalosporinase activities of *C. freundii* and *B. licheniformis* were both classified as strongly positive; the penicillinase activity and cephalosporinase activity of *B. cereus* were classified as moderately positive and negative, respectively (FIG. 5B and FIG. 6).

Activities of β-lactamases in 21 strains of 7 gram-positive species and 77 strains of 29 gram-negative species of bacteria were determined by the spot test, the HVE test, and the nitrocefin test after incubation for 1 hour at 37° C. (Table 1).

TABLE 1

Activities of β-lactamases of representative microorganisms determined by the spot test, the HVE test, and the nitrocelin test after incubation for 1 h at 37° C.

| | βlactamase acitivity[b] | | | | |
|---|---|---|---|---|---|
| | Spot test | | HVE test | | Nitro- |
| Microorganism[a] | P-ase | C-ase | P-ase | C-ase | celin test |
| GRAM-NEGATIVE ENTERIC | | | | | |
| *Citrobacter freundii* | | | | | |
| NRL5329 | + | + | S | S | + |
| ATCC 10787 | − | + | − | M | + |
| *Enterobacter aerogenes* | | | | | |
| NRL9817; ATCC13048 | − | + | − | M | + |
| *Enterobacter agglomerans* | | | | | |
| NRL9818; ATCC29915 | + | − | S | − | + |
| *Enterobacter cloacae* | | | | | |
| NRL5335, 9818: ATCC13047 | − | + | − | M | + |
| *Escherichia coli* | W | | | | |
| ATCC21986, 27549, 31027 | − | W | − | + | |
| *Klebsiella oxytoca* | | | | | |
| NRL9979 | + | − | S | − | + |
| *Klebsiella pneumoniae* | | | | | |
| NRL9976; ATCC13883, 27799 | + | − | S | − | + |
| *Morganella morganii* | | | | | |
| NRL5334; ATCC25830 | W | W | W | W | + |
| *Proteus mirabilis* | | | | | |
| ATCC14273, 29855 | W | W | W | W | − |
| *Proteus vulgaris* | | | | | |
| ATCC13315 | W | + | W | M | − |
| *Providencia rettgeri* | | | | | |
| ATCC9250, 31052 | − | − | − | − | − |
| *Salmonella typhimurium* | | | | | |
| ATCC13311 | − | − | − | − | − |
| *Serratia marcescens* | | | | | |
| ATCC8100, 17991 | − | + | − | S | + |
| *Serratia rubidaea* | | | | | |
| ATCC181 | W | + | W | S | + |
| *Shigella dysenteriae* | | | | | |
| ATCC13313 | − | W | − | W | + |
| *Shigella sonnei* | | | | | |
| ATCC11060 | − | + | − | M | + |
| GRAM-NEGATIVE NONENTERIC | | | | | |
| *Branhamella catarrhalis* | | | | | |
| NRL32674, 32681, 32763 | + | + | S | S | + |
| NRL30069, 30071, 32589 | − | − | − | − | − |
| *Eikenella corrodens* | | | | | |
| ATCC1073, 23834 | − | − | − | − | − |
| *Haemophilus ducreyi* | | | | | |
| V-1157, 1158, 1169 | + | + | S | M | + |
| V-1152, 1168 | − | − | − | − | − |
| *Haemophilus influenzae* | | | | | |
| AS1115, 902 | + | + | S | S | + |
| AS1117, E1a; ATCC19418 | − | − | − | − | − |
| *Neisseria gonorrhoeae* | | | | | |
| NRL33044, 33047, 33050 | + | + | S | S | + |
| NRL8327, 30483, F62 | − | − | − | − | − |
| *Pseudomonas aeruginosa* | | | | | |
| SM31302-31311 | W | W | W | W | − |
| *Pseudomonas cepaciae* | | | | | |
| BM1, 2 | + | + | S | S | + |
| *Pseudomonas fluorescens* | | | | | |
| BM3; ATCC25289 | − | + | − | S | + |
| *Pseudomonas maltophilia* | | | | | |
| BM4, 5; ATCC 13637 | + | + | S | S | + |

TABLE 1-continued

Activities of β-lactamases of representative microorganisms determined by the spot test, the HVE test, and the nitrocelin test after incubation for 1 h at 37° C.

| | βlactamase acitivity[b] | | | | |
|---|---|---|---|---|---|
| | Spot test | | HVE test | | Nitro- |
| Microorganism[a] | P-ase | C-ase | P-ase | C-ase | celin test |
| *Pseudomonas putida* | | | | | |
| BM6, 7; ATCC25571 | − | + | − | S | + |
| GRAM-NEGATIVE ANAEROBIC | | | | | |
| *Bacteroides bivius* | | | | | |
| ATCC29303 | + | + | S | M | 30 |
| *Bacteroides capillosus* | | | | | |
| ATCC29799 | − | − | − | − | − |
| *Bacteroides fragilis* | | | | | |
| ATCC23745, 25285 | W | + | W | M | + |
| GRAM-POSITIVE | | | | | |
| *Bacillus cereus* | | | | | |
| ATCC13061 | + | − | S | − | + |
| ATCC27348, 14579 | + | − | M | − | − |
| *Bacillus circulans* | | | | | |
| ATCC4513 | + | − | S | − | − |
| *Bacillus licheniformis* | | | | | |
| ATCC9789, 14409 | + | W | S | W | + |
| ATCC2572 | + | + | S | S | + |
| *Bacillus subtilis* | | | | | |
| ATCC9799, 14410 14415 | W | − | W | − | − |
| ATCC14807 | + | − | S | − | − |
| *Staphylococcus aureus* | | | | | |
| ATCC12598, 25923 | − | − | − | − | − |
| BM U17, Su3 | + | − | S | − | − |
| BM Mc19 | + | − | S | − | − |
| *Staphylococcus epidermidis* | | | | | |
| ATCC12228, 14990 | + | − | S | − | + |
| *Streptococcus faecalis* | | | | | |
| ATCC11420, 12984, 19433 − | − | − | − | − | |

[a]Strain numbers are those of the American Type Culture Collection (ATCC), The Neisseria Reference Laboratory (NRL), Stephen A. Morse (SM), Barbara H. Minshew (BM), and Arnold L. Smith (AS). Strains of *Haemophilus ducreyi* were described previously (19). The growth conditions for each microorganism were described under "Materials and Methods."

[b]The activities of penicillinase (P-ase) and cephalosporinase (C-ase) in each microorganism determined by the spot test and by the HVE test were recorded as follows: The spot test result for β-lactamase activity using a given substrate was classified as weakly positive (W) when the fluorescent intensity of the spot was faint but discernably greater than that of the uninoculated substate control; and as positive (+) when bright, blue-green flourescence was observed. The HVE test result for β-lactamase activity using a given substrate was classified as weakly positive (W) when faint fluorescence was observed at the position corresponding to that of the end product after HVE, and the color intesisty of the end product spot after ninhydrin-cadmium acetate stain was slightly but discernably greater than that of the end product in the uninoculated substrate control (produced by spontaneous nonenzymatic hydrolysis and from contamination); as moderately positive (M), when bright, blue-green flouorescence was observed at the position corresponding to that of the end product spot but color intensity of the end product spot after ninhydrin-cadmium acetate stain was less than that of the remaining substrate spot; as strongly positive (S) when bright, blue-green flourescence was abserved at the position corresponding to that of the end product spot and the color intensity of the end product spot after ninhydrin-cadmium acetate stain was greater than that of the remaining substrate spot.

The results of the nitrocefin test agreed well with those of the spot test (confirmed by the HVE test). Some beta-lactamases which acted predominately against ampicillin, such as a few species of gram-positive bacteria, were not detected by the nitrocefin test. Therefore, the fluorescent method disclosed herein was more sensitive than the chromagenic cephalosporin (nitrocefin) method. Activities of beta-lactamases in selected beta-lactamase producers listed in Table 1 were further assessed by the rapid spot test and the nitrocefin test after incubation for 5 and 15 minutes at room temperature, the results listed in Table 2.

TABLE 2

Activities of β-lactamases of selected microorganisms determined by the raped spot test and the nitrocelin test after incubation for 5 and 15 min at room temperature

| | β-lactamase activity[b] | | | | | |
|---|---|---|---|---|---|---|
| | Incubation time | | | | | |
| | 5 Min | | 15 Min | | Nitrocelin test Incubation time | |
| Microorganism[a] | P-ase | C-ase | P-ase | C-ase | 5 Min | 15 Min |
| GRAM-NEGATIVE | | | | | | |
| ENTERIC | | | | | | |
| *Citrobacter freundii* | | | | | | |
| NRL5329 | + | + | + | + | + | + |
| ATCC 10787 | − | − | − | + | − | + |
| *Enterobacter aerogenes* | | | | | | |
| NRL9817, ATCC13048 | − | − | − | + | − | − |
| *Enterobacter agglomerans* | | | | | | |
| NRL9819; ATCC29915 | + | − | + | − | − | + |
| *Enterobacter cloacae* | | | | | | |
| NRL5335, 9818; ATCC13047 | − | − | − | + | − | − |
| *Klebsiella oxytoca* | | | | | | |
| NRL9979 | + | − | + | − | − | − |
| *Klebsiella pneumoniae* | | | | | | |
| NRL9976; ATCC13883 | + | − | + | − | − | − |
| *Serratia marcescens* | | | | | | |
| ATCC8100, 17991 | − | − | − | + | − | + |
| *Serratia rubidaea* | | | | | | |
| ATCC181 | − | − | − | − | − | − |
| *Shigella sonnei* | | | | | | |
| ATCC11060 | − | − | − | + | − | − |
| GRAM-NEGATIVE NONENTERIC | | | | | | |
| *Branhamella catarrhalis* | | | | | | |
| NRL32674, 32681, 32763 | + | − | + | − | + | + |
| *Haemophilus ducreyi* | | | | | | |
| V-1157, 1158, 1169 | + | − | + | − | + | + |
| *Haemophilus influenzae* | | | | | | |
| AS1115, 902 | + | − | + | − | + | + |
| *Neisseria gonorrhoeae* | | | | | | |
| NRL33044, 33047, 33050 | + | − | + | − | + | + |
| *Pseudomonas cepaciae* | | | | | | |
| BM1, 2 | − | − | − | + | − | + |
| *Pseudomonas fluorescens* | | | | | | |
| BM3; ATCC25289 | − | − | − | + | − | + |
| *Pseudomonas maltophilia* | | | | | | |
| BM4, 5 | + | + | + | + | + | + |
| *Pseudomonas putida* | | | | | | |
| BM6,7; ATCC25571 | − | − | − | + | − | + |
| GRAM-POSITIVE | | | | | | |
| *Bacillus cereus* | | | | | | |
| ATCC13061 | + | − | + | − | + | + |
| ATCC27348, 14579 | − | − | + | − | − | − |
| *Bacillus circulans* | | | | | | |
| ATCC4513 | − | − | W | − | − | − |
| *Bacillus licheniformis* | | | | | | |
| ATCC9789, 14409 | − | − | + | W | − | + |
| ATCC 25972 | + | − | + | + | + | + |
| *Bacillus subtilis* | | | | | | |
| ATCC14807 | − | − | + | − | − | − |
| *Staphylococcus aureus* | | | | | | |
| BM U17, Su3 | − | − | + | − | − | + |
| BM Me19 | − | − | + | − | − | − |
| *Staphylococcus epidermidis* | | | | | | |
| ATCC14990 | + | − | + | − | + | + |
| ATCC1228 | − | − | + | − | − | + |

[a]Strain numbers are those of the American Type Culture Collection (ATCC), The Neisseria Reference Laboratory (NRL), Stephen A. Morse (SM), Barbara H. Minshew (BM), and Arnold L. Smith (AS). Strains of *Haemophilus ducreyi* were described previously (19). The growth conditions for each microorganism were described under "Materials and Methods."

[b]The activites of penicillinase (P-ase) and cephalosporinase (C-ase) in each microorganism determined by the spot test were recorded as follows: The spot test reult for β-lactamase activity using a given substrate was classified as weakly positive (W) when the fluorescent intensity of the spot was fain but discernably greater than that of the uninoculated substrate control; and as postive when bright, blue-greem flourescence was observed.

The incubation time needed for a positive reaction for the fluorescent spot test appeared to be about the same as, or shorter than, that needed for the nitrocefin test. Some clinically important microorganisms, such as *N. gonorrhoeae* and *H. influenzae*, produce beta-lactamases which could be detected by the rapid spot test immediately after the organisms were suspended in the ampicillin substrate solution, without further incubation. The fluorescent spot test detection method described herein can not only distinguish beta-lactamase activity from acylase activity, but also can detect and differentiate between penicillinase activity and cephalosporinase activity. The fluorescent spot test may require 5 minutes of heating at 120° C. to maximize the fluorescent potential of the end products, although the mechanism by which heating enhances fluorescence is not fully understood.

The beta-lactam antibiotic substrate solutions (acid forms) were prepared in 0.04M sodium phosphate buffer, pH 7.5.

These solutions both had a pH of 7.0. The pH of both solutions fell to 6.5 [within the optimal pH ranges of microbial beta-lactamases (Sykes, R. B., and M. Matthew, "Detection, Assay and Immunology of Beta-lactamases," *Beta-lactamases*, 17–49 (1979), J. M. T. Hamilton-Miller and J. T. Smith (eds.), Academic Press, New York)], upon complete hydrolysis by *C. freundii*, and could be stored at 4° C. for 5 days or −20° C. for several months without detectable increases in fluorescent background as checked by the spot test.

Some organisms fluoresced slightly on paper, but this fluorescence was confined to the center of the applied spot, and could be easily distinguished from the fluorescence of end products which diffuse radially by capillary action of the paper from the center of application. Therefore, the spot test can be performed without prior removal of the organisms by centrifugation.

Unless the beta-lactamase sought shows no substrate specificity, the ampicillin and cephalexin substrates should be incubated separately with the organism. When penicillin and cephalosporin substrates are mixed together, the substrate which is not hydrolyzed may act as a competitive inhibitor of the other substrates. For example, *S. marcescens* (ATCC 8100 and 17991) exhibits only cephalpsporinase activity, as detected by the spot test and the HVE test, when ampicillin and cephalexin are incubated separately with the organism. However, cephalosporinase activity was not detected in either organism by the spot test or the HVE test when both strains were incubated with a mixture of equal volumes of ampicillin and cephalexin substrate solution for 1 hour at 37° C.

The detection method, or spot test, described herein, using ampicillin and cephalexin as substrates provides a rapid and inexpensive method for the specific detection of microbial beta-lactamases by detecting the presence of fluorescent end products. This detection method may have several applications. For example, incubation with human sera can result in a color change for nitrocefin. Therefore, nitrocefin is not suitable for detection of beta-lactamase in the presence of certain body fluids. It was found that eight out of eight human sera converted nitrocefin to a red color after 20 minutes incubation at 37° C., but produced no fluorescence after incubation with ampicillin and cephalexin for 1 hour at 37° C. In contrast, the methods described herein have the potential for the direct detection of microbial beta-lactamases in clinical specimens.

The detection of fluorescent end products utilizing the method described herein also offers an economical alternative for clinical laboratories which test large numbers of microorganisms for beta-lactamases. For example, the routine beta-lactamase test on staphylococcal isolates using nitrocefin require a noninhibitory concentration of a semisynthetic penicillin as an inducer for the enzyme.

TABLE 3

Activities of β-lactamases of selected microorganisms determined by the fluorescent spot test with fluorescence developer solution after incubation for 5 min at 50° C. and 15 min at 37° C.

| Microorganisms | β-Lactamase activity by[b]: Fluorescent spot test with incubation for: | | | |
|---|---|---|---|---|
| | 5 min at 50° C. | | 15 min at 37° C. | |
| | Penicillinase | Cephalosporinase | Penicillinase | Cephalosporinase |
| Gram-negative enteric bacteria | | | | |
| *Citrobacter freundii* | | | | |
| NRL 5329 | + | + | + | + |
| ATCC 10787 | − | + | − | + |
| *Enterobacter cloacae* | | | | |
| NRL 5335 | − | + | − | + |
| ATCC 13047 | − | + | − | + |
| *Klebsiella oxytoca* | | | | |
| NRL 9979 | + | − | + | − |
| *Klebsiella pneumoniae* | | | | |
| NRL 9976 | + | − | + | − |
| ATCC 13883 | + | − | + | − |
| *Serratia marcescens* | | | | |
| ATCC 8100 | − | + | − | + |
| ATCC 17991 | − | + | − | + |
| *Shigella sonnei* | | | | |
| ATCC 11060 | − | + | − | + |
| Gram-negative nonenteric bacteria | | | | |
| *Haemophilus ducreyi* | | | | |
| V-1157 | + | + | + | + |
| V-1158 | + | + | + | + |
| *Haemophilus influenzae* | | | | |
| AS1115 | + | + | + | + |
| AS902 | + | + | + | + |
| *Neisseria gonorrhoeae* | | | | |
| NRL 33044, 33047, 33050 | + | + | + | + |
| NRL F62, 33, Mcl | − | − | − | − |
| *Pseudomonas cepaciae* | | | | |
| BM1 | + | + | + | + |
| BM2 | + | + | + | + |
| *Pseudomonas maltophilia* | | | | |
| BM4 | + | + | + | + |
| BM5 | + | + | + | + |
| Gram-positive bacteria | | | | |
| *Bacillus cereus* | | | | |
| ATCC 13061 | + | + | + | + |
| ATCC 14579 | + | − | + | − |
| *Bacillus licheniformis* | | | | |
| ATCC 9789 | W | − | + | + |
| ATCC 25972 | + | + | + | + |
| *Bacillus subtilis* | | | | |
| ATCC 14807 | W | − | + | − |
| *Staphylococcus aureus* | | | | |
| BMSu3 | + | + | + | + |
| BMMe19 | + | − | + | − |

Strain numbers are those of the American Type Culture Collection (ATCC), the Neissertia Reference Laboratory (NRL), Barbara H. Minshew (BM) and Arnold L. Smith (AS), Strains of *H. ducresi* and the growth conditions for each microorganism were previously described in the co-pending patent
[b]The activities of penicillinase and cephalosporinase in each microorganism as determined by the fluorescent spot test were recorded as follows. The spot test result for β-lactamase activity using a given substrate was classified as weakly positive (W) when the fluorescent intensity of the spot was faint but discernibly brighter than that of the uninoculated substrate control: the result was positive when bright, blue-green fluorescence was observed. Both ampicillin (for penicillinase activity) and cephalexin (for cephalosporinase activity) were used at a concentration of 1 mM and 10 mM, respectively, ml as described in Materials and Methods.

In the present fluorescent spot test method, with sufficient incubation time (e.g., ≧15 minutes), ampicillin could serve not only as a substrate, but also as an inducer for these gram-positive bacteria of clinical importance.

EXAMPLE II

MATERIALS

Chemicals

Chemicals and reagents utilized in this example were purchased as described in Example I. The solutions of beta-lactam antibiotics, their side chains, and beta-lactam nuclei were prepared as previously described in Example I, except that all the β-lactam antibiotic substrates were prepared in 20 mM sodium phosphate buffer (pH 7.3) for a final concentration of either 1 mM or 10 mM (pH was adjusted to 7.0).

METHODS

Hydrolysis of Beta-lactam Antibiotics by Purified Beta-lactamase

Penicillin substrates (ampicillin and amoxicillin) were hydrolyzed by beta-lactamase from *Bacillus cereus* (Sigma Chemical Co., St. Louis, Mo.). 100 nmol of each substrate was incubated with 0.25 μg of beta-lactamase for 1 hour at 37° C. Cephalosporin substrates (cephaloglycin, cephalexin and cefadroxil) were hydrolyzed with beta-lactamase from *Enterobacter cloacae* (Sigma Chemical Co.). 100 nmol of each substrate was incubated with 8 μg of beta-lactamase for 1 hour at 37° C. The extent of hydrolysis was monitored by two-dimensional, thin-layer chromatography on polyamide sheets after dansylation of the reaction mixture as described in (Chen, K. C. S., "Two-dimensional thin-layer chromatography for simultaneous detection of microbial β-lactam acylases and β-lactamases," *Antimicrob. Agents Chemother.* 30: 536–541, 1986).

Preparation of Improved Developer Solutions

Developer I was prepared by adding AgNO$_3$ to sodium citrate buffer to a final concentration of 1.1 mM Ag$^+$. Formaldehyde was added to sodium citrate buffer solution to a final concentration of 1.1M. pH of the sodium citrate buffer (1.1M) was adjusted to 4.0 after addition of AgNO$_3$ and formaldehyde.

Developer II was prepared by adding HgCl$_2$ to sodium citrate buffer to a final concentration of 1.1 mM. Formaldehyde was added to sodium citrate buffer solution to a final concentration of 1.1M. The sodium citrate buffer (1.1M) was adjusted to a pH of 4.0. Addition of 1 volume of either developer I or developer II to 10 volumes of β-lactam antibiotic substrate solution incubated with β-lactamase-producing organisms was used for fluorescence development.

Preparation of Inocula for Detection of Beta-lactamase

The growth conditions for each microorganism used in this example were the same as those utilized in Example 1. A portion (200 ml) of each β-lactam antibiotic substrate solution was separately placed in a disposable culture tube (10×75 mm). A cotton-tipped applicator which contained approximately one-half of a loopful (diameter, 2 mm) of growth of each strain removed from the agar plate was mixed in each substrate tube and incubated for 5 minutes at 50° C. or 15 minutes at 37° C. Uninoculated substrate controls were prepared in the same manner.

Fluorescent Spot Test for the Detection of Microbial β-lactamases Using the Improved Fluorescence Developer After 5 minutes of incubation at 50° C. or 15 minutes at 37° C., 20 μl of fluorescence developer solution was added to each tube, including each uninoculated substrate control tube. The reaction mixture was mixed briefly with the applicator and further incubated at 50° C. (water bath) for 5 minutes. After the incubation, the applicator from each tube, including each uninoculated substrate control tube, was separately touched onto a Whatman 3 MM filter paper to form a spot with a diameter of about 8 mm. The fluorescent intensity of each spot was then compared with its uninoculated substrate control spot under a long-wave UV lamp and classified as negative, weakly positive, or positive.

Comparison of Hydrolytic Rates of Ampicillin and Cephalexin Substrates by a Given Organism at 37° C.

For comparison of rates of hydrolysis of ampicillin and cephalexin substrates by a given organism, a 100 μl aliquot of each beta-lactam substrate solution was separately placed in a disposable 10×75 ml borosilicate culture tube. A 2 mm diameter loopful of growth of each strain was removed from the agar plate containing the organisms to be tested. These samples were suspended in 200 μl of normal saline by vortexing. Ten μl of each twofold dilution of bacterial suspension in normal saline was added separately to each substrate solution. After incubation at 37° C. for 30 minutes, 11 μl of fluorescence developer solution was added. The reaction mixture was further incubated at 50° C. in a water bath for 5 minutes. The reaction mixtures were separately transferred to a Nunc-Immune Plate II (96 wells, Scientific Resource Associates, Bellevue, Wash.). These samples were twofold serially diluted in water with a 12-channel pipette (Flow Laboratories, Inc., Inglewood, Calif.). Five μl samples from each well were spotted on a Whatman 3 MM with the 12-channel pipette and viewed under a long-wave UV lamp.

Comparison of Hydrolytic Rates of Ampicillin or Cephalexin Substrate by a Given Organism at 37° C. and 50° C.

The procedure for comparison of rates of hydrolysis of ampicillin or cephalexin at 37° C. and at 50° C. by a given organism is determined as described above, except that a single substrate solution was used and incubations were carried out separately at 37° C. and 50° C.

Figure 7:
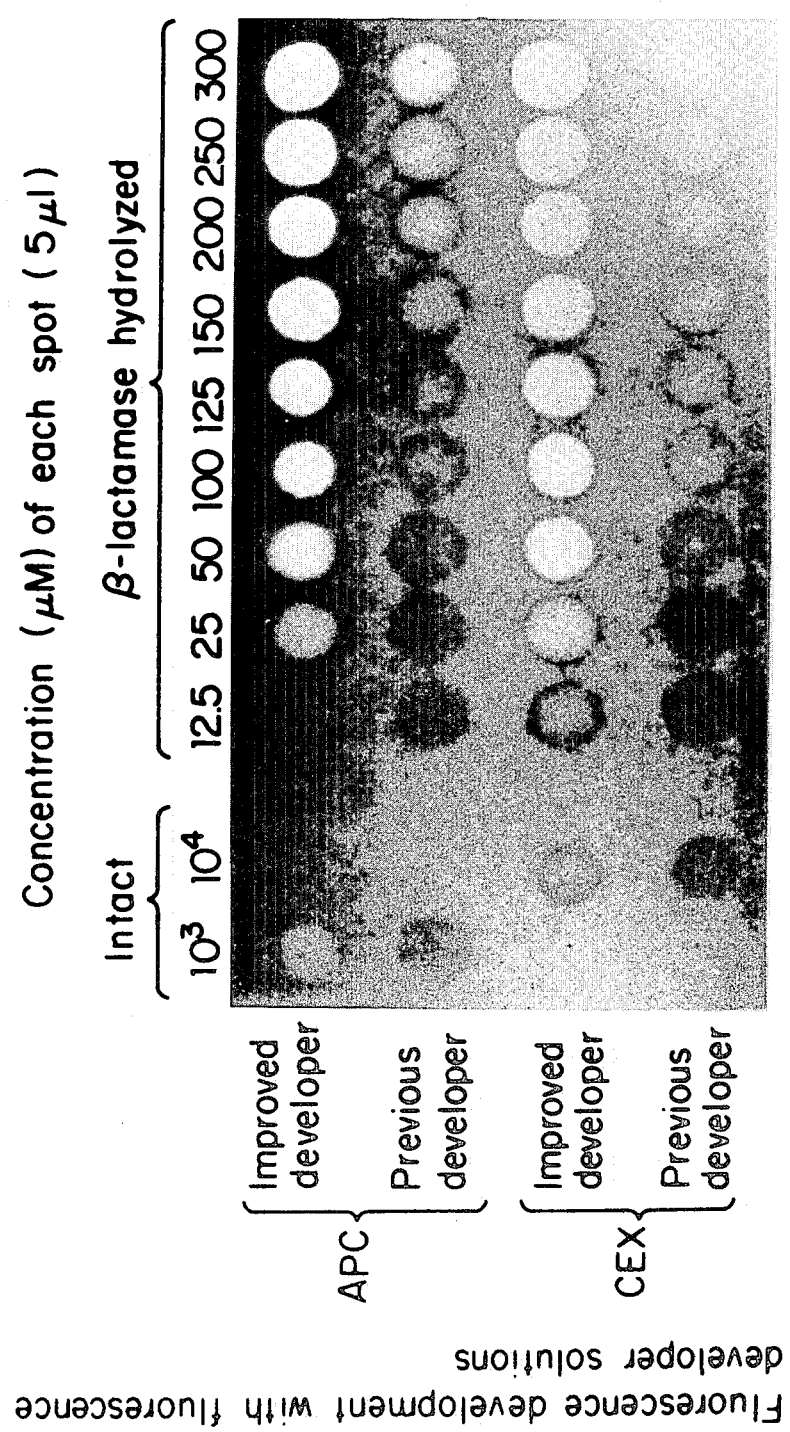
FIG. 7 depicts data comparing detection of beta-lactamase activity utilizing the improved developer of the present invention and comparing it to the developer described in Chen, K. C. S., and K. K. Holmes. *J. Clin. Microb.* 23: 539–544, 1986. APC=ampicillin; CEX=cephalexin.

Fluorescence Development of End Products Resulting from Beta-lactamase Hydrolysis by Use of the Improved Fluorescence Developer Solutions Substrate solutions of penicillins (ampicillin and amoxicillin) and cephalosporins (cephaloglycin, cephalexin, and cefadroxil) were not fluorescent under UV light. The solutions of their corresponding open β-lactam ring end products resulting from β-lactamase hydrolysis also were not fluorescent under UV light. After addition of the improved fluorescence developer of this invention, to the intact substrates and their corresponding open β-lactam ring end products, followed by heating each reaction mixture at 50° C. for 5 minutes, only the end products became fluorescent. For example, as shown in FIG. 7, after addition of fluorescence developer II and heating at 50° C. for 5 minutes, fluorescence developed only for the end products of ampicillin or cephalexin after β-lactamase hydrolysis. Developer I produced similar results.

Figure 8:
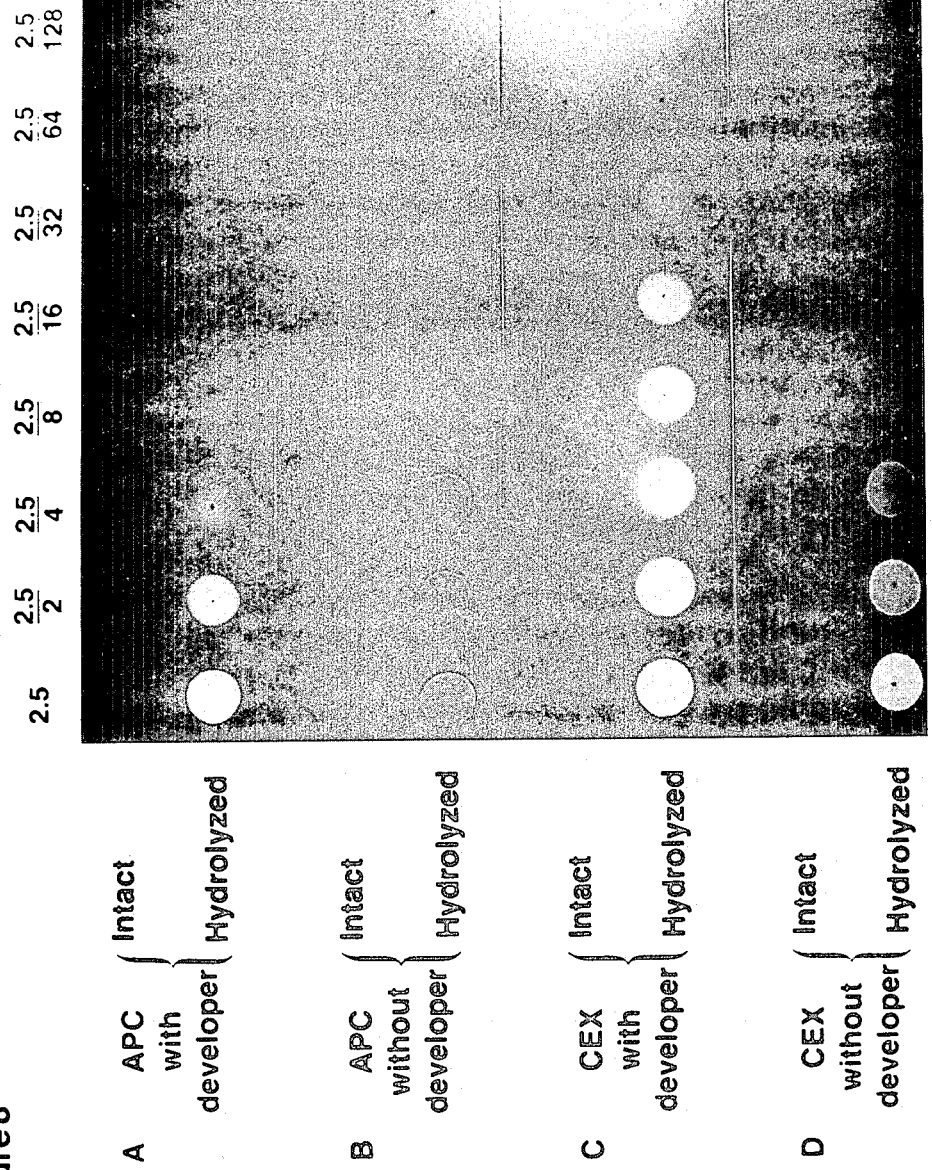
FIG. 8 illustrates data comparing the detection of beta-lactamase activity utilizing the previously described developer of FIG. 7 and comparing it to fluorescence development without a developer.

Improvement of Fluorescence Development with the Improved Fluorescence Developer The fluorescent intensity of end products produced by β-lactamase with the developer described in *J. Clin. Microb.* 23: 539–544, 1986, was about 4-fold and 16-fold greater for ampicillin and cephalexin substrates, respectively, than the fluorescent intensity of the fluorescent spot test without a fluorescence developer (see FIG. 8). The fluorescent intensity of end products produced by β-lactamase with the improved fluorescence developer (developer II) as described in this invention was about 10-fold and 6-fold greater for ampicillin and cephalexin substrates, respectively, than the fluorescent intensity of the fluorescent spot test with a developer described in *J. Clin. Microb.* 23: 538–544, 1986. Therefore, the overall fluorescent intensity of end products produced by β-lactamase with the improved fluorescence developer described in this invention was approximately 40-fold and 96-fold greater for ampicillin and cephalexin substrates, respectively, than the fluorescent intensity without a fluorescence developer, as described in Example I.

Figure 9:
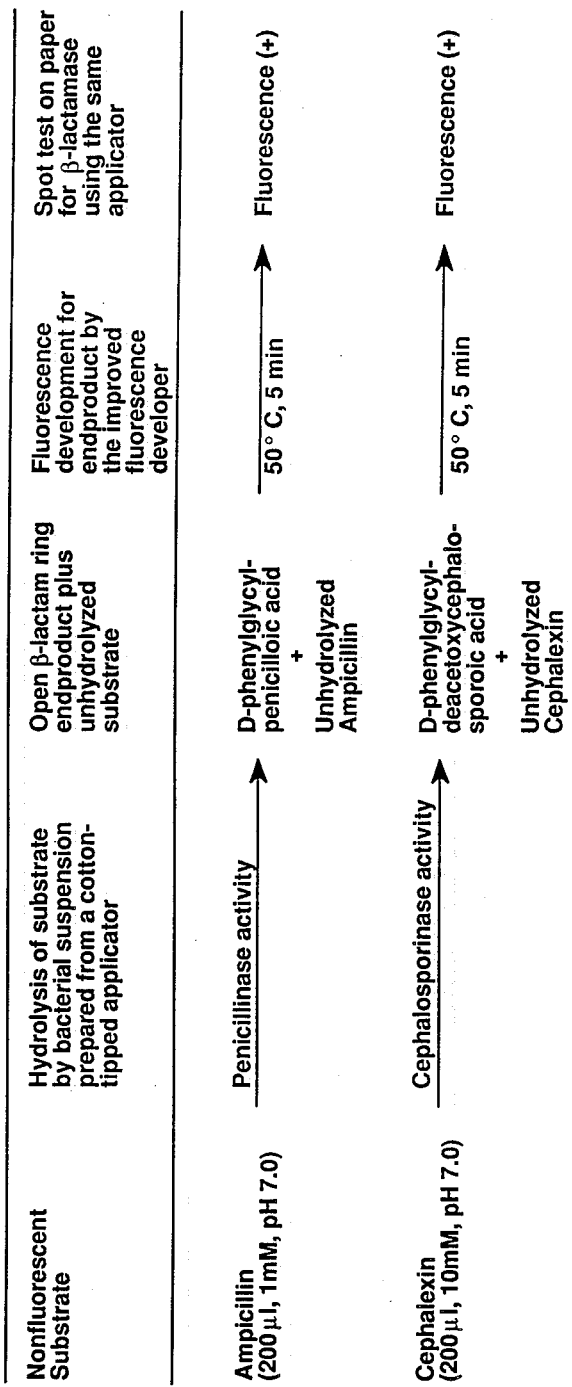
FIG. 9 is a summary of the steps in the fluorescent spot test for the detection of microbial beta-lactamases by the use of the improved fluorescence developer as described in the present invention.

Differentiation Between β-lactamase and Acylase Activities and Between Penicillinase and Cephalosporanase Activities of β-lactamase by the Fluorescent Spot Test with the Improved Fluorescence Developer Whether the fluorescent spot test using the improved fluorescence developer of this invention could distinguish β-lactamase activity from acylase activity was determined. Solutions of the end products of acylase activity upon ampicillin, cephaloglycin, and cephalexin (the common acyl side chain D(−)-α-aminophenylacetic acid and the intact β-lactam nuclei 6-aminopenicillanic acid, 7-aminocephalosporanic acid, and 7-aminodeacetoxycephalosporanic acid, respectively) and upon amoxicillin and cefadroxil (the common acyl side chain D(−)-p-hydroxyphenylglycine and the intact β-lactam nuclei, 6-aminopenicillanic acid, and 7-aminodeacetoxycephalosporanic acid, respectively) were not fluorescent after the addition of the improved fluorescence developer and heating at 50° C. for 5 minutes. Therefore, when ampicillin, amoxicillin, cephaloglycin, cephalexin or cefadroxil was used as a substrate for β-lactamases activity, the fluorescent spot test with the improved fluorescence developer of this invention, could distinguish β-lactamase activity from acylase activity. Ampicillin was chosen to detect penicillinase activity because it produced less fluorescent background than amoxicillin, and cephalexin was chosen to detect cephalosporinase activity because it produced less fluorescent background than cephaloglycin and cefadroxil. The steps in the fluorescent spot test for detection of microbial β-lactamases with the improved fluorescence developer are summarized in FIG. 9.

Detection of β-lactamases Among the Selected Microorganisms

The spot test result for β-lactamase activity with a given substrate was classified as weakly positive when the fluorescent intensity of the spot was faint but discernibly brighter than that of the uninoculated substrate control and as positive when bright blue-green fluorescence was observed. The spot test with the improved fluorescence developer (developer II) was used for the detection of β-lactamases produced by 24 strains of 11 gram-negative species and 7 strains of 4 gram-positive species with ampicillin (for penicillinase activity) and cephalexin (for cephalosporinase activity) as substrates after an incubation for 5 minutes at 50° C. or 15 minutes at 37° C. For gram-negative bacteria, the sensitivity of the fluorescent spot test conducted at 50° C. for 5 minutes was essentially the same as that of the same test conducted at 37° C. for 15 minutes. For some of the gram-positive bacteria, the test was more sensitive when conducted at 37° C. for 15 minutes. Presumably substrate induction is required for these organisms (Table 3).

Figure 10:
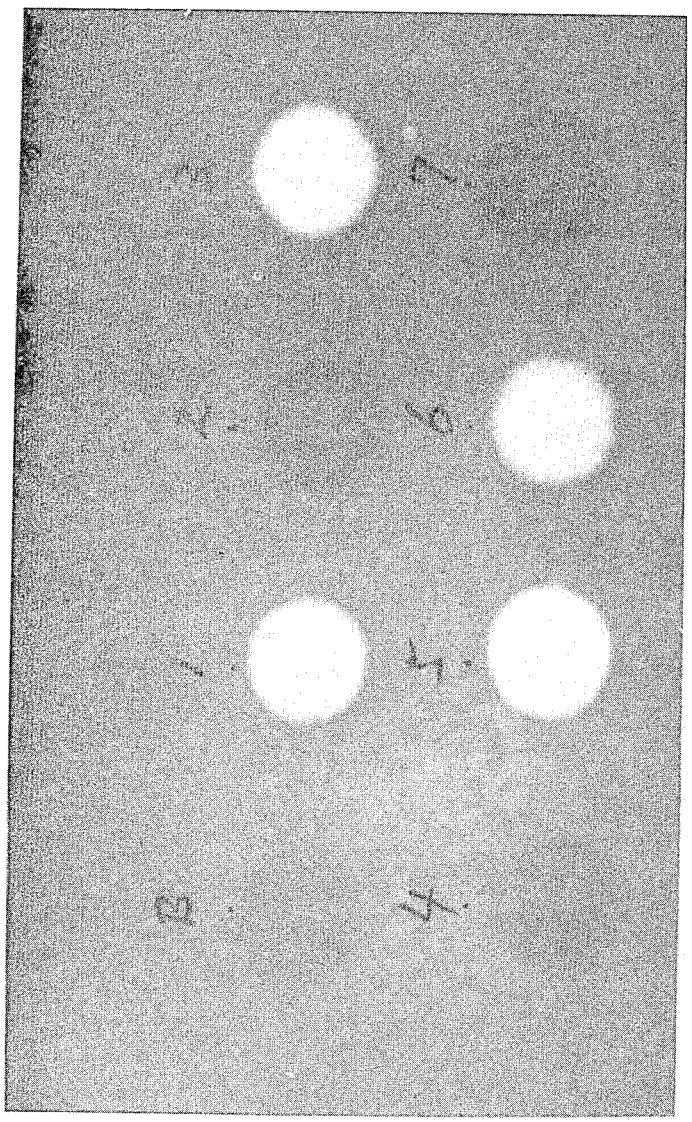
FIG. 10 depicts the penicillinase activity in PPNG strains using the improved fluorescence developer for fluorescence development.

For the detection of β-lactamases in a known organism, the optimum substrate and incubation temperature can be pre-selected as described below. FIG. 10 shows the penicillinase activity in PPNG strains after incubation with ampicillin for 1 minute at 50° C. using the improved fluorescence developer (developer II) for the fluorescence development of the end products.

Visual Quantitation of End Products Resulting from Beta-lactamase Hydrolysis

Based upon the fact that the fluorescent intensities of the spots of the end products with concentrations of more than 200 μM became indistinguishable when the improved developer is used for fluorescence development (FIG. 7), a visual quantitation of the end products was designed by comparing the fluorescent intensities of the spots from twofold serially diluted reaction mixtures. The data are shown in Table 4.

TABLE 4

Visual quantitation of the end products resulting from β-lactamase hydrolysis of ampicillin and cephalexin

| Percentage of beta-lactam substrate hydrolyzed by beta-lactamase | Comparison of fluorescent intensities of the spots of twofold serially diluted reaction mixtures | | | | | | | |
|---|---|---|---|---|---|---|---|---|
| | APC 1 mM | | | | CEX 10 mM | | | |
| | 1 | 2 | 4 | 8 | 1 | 2 | 4 | 8 |
| CEX >16 | | | | | = | = | > | = |
| APC ≧80; CEX≧8 | = | = | > | | = | = | > | |
| 40 ≦APC <80; 4≦CEX <8 | = | > | > | | = | > | > | |
| APC <40; CEX <4 | > | > | > | | > | > | > | |

Figure 11:
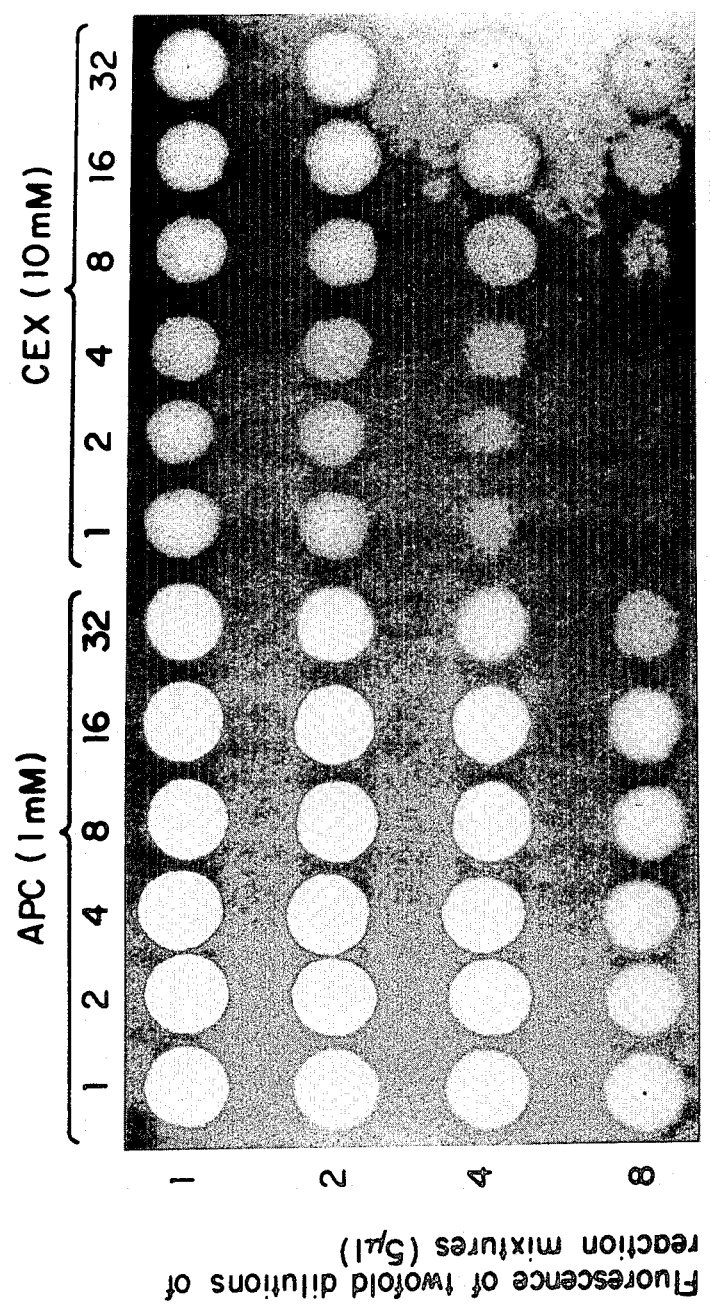
FIG. 11 depicts comparative fluorescent data for 1 mM ampicillin and 10 mM cephalexin hydrolyzed by a strain of penicillinase-producing *Neisseria gonorrhoeae* (PPNG).

Selection of an Optimal Substrate for Detection of Microbial Beta-lactamase with Known Origin Employing the improved developer of the present invention, selection of an optimum substrate for beta-lactamase which exhibits a predominance of either penicillinase activity of cephalosporinase activity is relatively straightforward. However, selection of an optimum substrate for beta-lactamase where penicillinase activity and cephalosporinase activity are comparable is difficult. In this case, the fluorescent spot test utilizing prior art methodologies results in indistinguishable intensities of fluorescence. Twofold serially diluted bacterial suspensions from an organism with ampicillin and cephalexin substrates were separately incubated and treated with developer. The fluorescence of the end products resulted from beta-lactamase hydrolysis, which could be visually quantitated after twofold dilutions of the reaction mixtures, as shown in Table 4. Twofold serially diluted bacterial suspensions from a strain of penicillinase-producing Neisseri gonorrhoeae (PPNG) were incubated separately with 1 mM ampicillin and 10 mM cephalexin. Fluorescence of the end products was visually quantitated by twofold dilutions of the reaction mixture, as shown in FIG. 11.

Fluorescent intensities of spots from the non-diluted and 2-fold and 4-fold diluted reaction mixtures after incubations of the non-diluted and 2-fold, 4-fold, 8-fold and 16-fold diluted bacterial suspensions with 1 mM ampicillin substrate were almost indistinguishable, indicating more than 80% of each ampicillin substrate solution was hydrolyzed by each bacterial suspension (Table 4). Fluorescent intensities of spots from the non-diluted and 2-fold, 4-fold and 8-fold diluted reaction mixtures were successively decreased with increasing dilutions after incubations of the non-diluted and all the twofold serially diluted bacterial suspensions with 10 mM cephalexin substrate, indicating less than 4% of each cephalexin substrate solution was hydrolyzed by each bacterial suspension (Table 4). Therefore, ampicillin was the preferred substrate for detection of β-lactamase in PPNG.

Therefore, utilization of the improved developer of the present invention permits determination of the optimum substrate for PPNG utilizing visual analysis of fluorescent spot. This is especially true where penicillinase and cephalosporinase activities are comparable.

Selection of Incubation Temperature for Detection of Microbial Beta-lactamases

Figure 12:
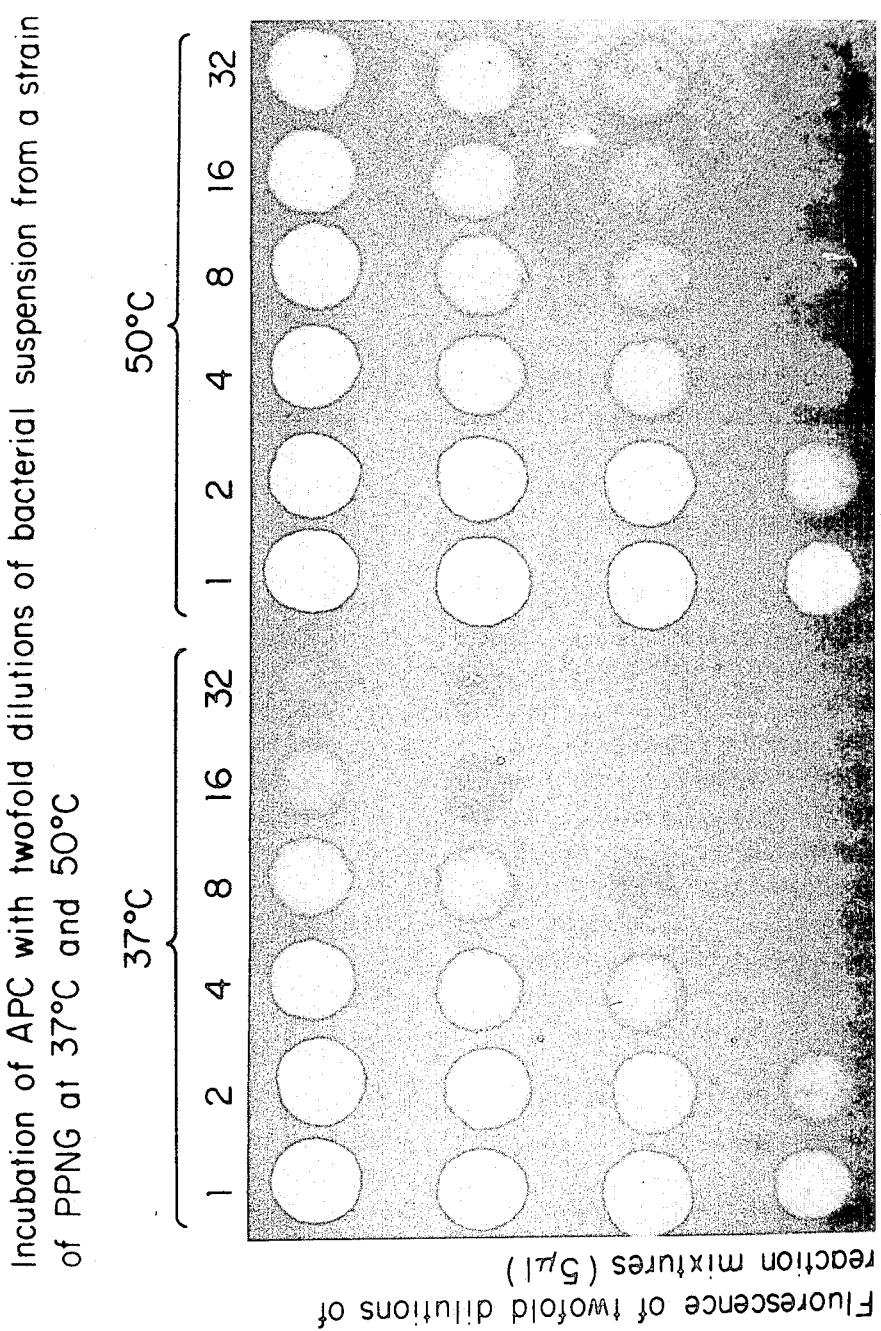
FIG. 12 depicts data comparing the effect of incubation temperature on β-lactamase activity in PPNG.

Selection of an optimum temperature for incubation of a selected substrate with an organism is important for rapid detection of microbial beta-lactamases. For example, ampicillin was selected for detection of beta-lactamase activity in a strain of PPNG, as described above. Fluorescent intensities of spots of the non-diluted and 2-fold, 4-fold and 8-fold diluted reaction mixtures after incubations of the 4-fold, 8-fold, 16-fold and 32-fold diluted bacterial suspensions with 1 mM ampicillin substrate were significantly greater when incubations were carried out at 50° C. for 5 minutes than those carried out at 37° C. for 5 minutes (FIG. 12). Therefore, the preferred temperature for detection of beta-lactamase activity in the same strains of PPNG was determined to be 50° C.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method of detecting the presence of beta-lactamase from microbial sources using a beta-lactam ring containing substrate whose amide bond is hydrolyzed in the presence of beta-lactamase, comprising:
    (a) contacting a substantially nonfluorescent substrate which includes a beta-lactam ring with an acyl side chain containing an alpha-amino group an alpha-phenyl group or its derivatives, with an organism thought to produce beta-lactamase or with a cell-free preparation thought to contain beta-lactamase, to produce a reaction mixture;

(b) contacting said reaction mixture with a fluorescence developer solution comprising an oxidizing agent in buffer; and (c) determining whether the reaction product from said substrate, said oxidizing agent, and said organism or said preparation fluoresces as a result of beta-lactamase hydrolysis of said substrate.

2. The method of claim 1 wherein the solution containing the oxidizing agent is selected from the group consisting of Ag+, Hg++, H$_2$O$_2$, I$_3$—, IO$_4$, persulfate, Pd++, and p-hydroxymercuribenzoate.

3. The method of claim 2 wherein the solution containing the oxidizing agent additionally comprises formaldehyde in a concentration ranging from approximately 0.22M to approximately 2.2M.

4. The method of claim 1 wherein the buffer includes the salt of citric acid, tartaric acid, malic acid, succinic acid, glutaric acid, lactic acid, or phthalic acid.

5. The method of claim 1 wherein the pH of the fluorescence developer solution is about 3.5 to 5.5.

6. The method of claim 1 wherein the substantially nonfluorescent substrate is selected from the group consisting of ampicillin, amoxicillin, cephaloglycin, cephalexin, hetacillin, and cefadroxil.

7. The method of claim 1 wherein step (b) is performed at a temperature between 22° C. and 50° C.

* * * * *